United States Patent [19]

Love, III

[11] Patent Number: 4,533,245
[45] Date of Patent: Aug. 6, 1985

[54] INSPECTION LIGHTING SYSTEM

[75] Inventor: Franklin S. Love, III, Spartanburg, S.C.

[73] Assignee: Milliken Research Corporation, Spartanburg, S.C.

[21] Appl. No.: 429,957

[22] Filed: Sep. 30, 1982

[51] Int. Cl.³ .................. G01N 21/47; G01N 21/88
[52] U.S. Cl. ............................. 356/238; 356/430; 356/446; 26/70
[58] Field of Search ............ 356/237, 238, 429, 430, 356/431, 445, 446, 376; 26/70; 250/562, 563, 571, 572

[56] References Cited

U.S. PATENT DOCUMENTS

| | | | |
|---|---|---|---|
| 2,059,308 | 2/1934 | Boadwee et al. | 356/238 |
| 3,524,988 | 11/1967 | Gaither, IV | 356/238 |
| 3,574,469 | 4/1971 | Emerson | 26/70 |
| 3,877,814 | 4/1975 | Hess et al. | 356/430 X |
| 3,992,111 | 11/1976 | Roulier et al. | 356/431 |
| 4,065,213 | 12/1977 | Nyman | 26/70 |

Primary Examiner—Vincent P. McGraw
Assistant Examiner—S. A. Turner
Attorney, Agent, or Firm—H. William Petry; George M. Fisher

[57] ABSTRACT

A method and apparatus for inspecting substrates such as flat textile fabrics which have been sculptured to a depth of less than about 0.003 inches. Opposing line sources of illumination are used to illuminate the substrate at a relatively low angle while the substrate is held flat in front of a dark, non-reflective background and is substantially shielded from ambient light.

7 Claims, 2 Drawing Figures

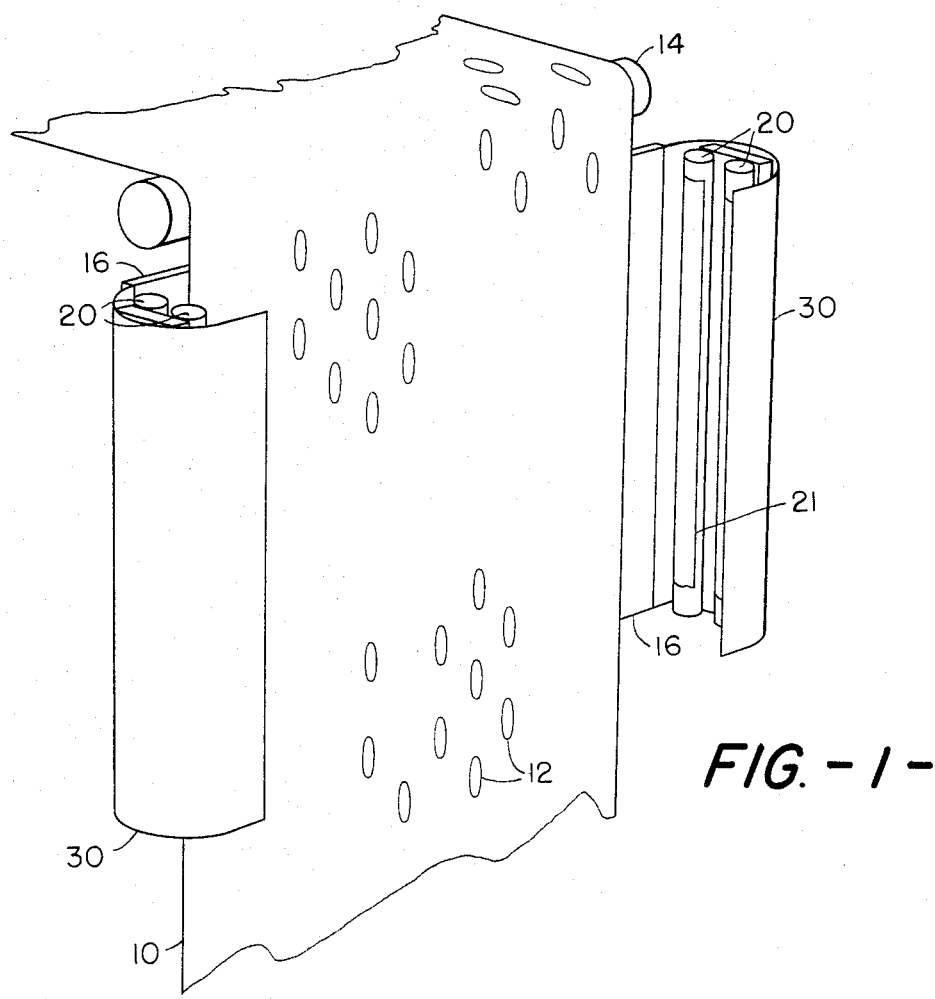
FIG. -1-
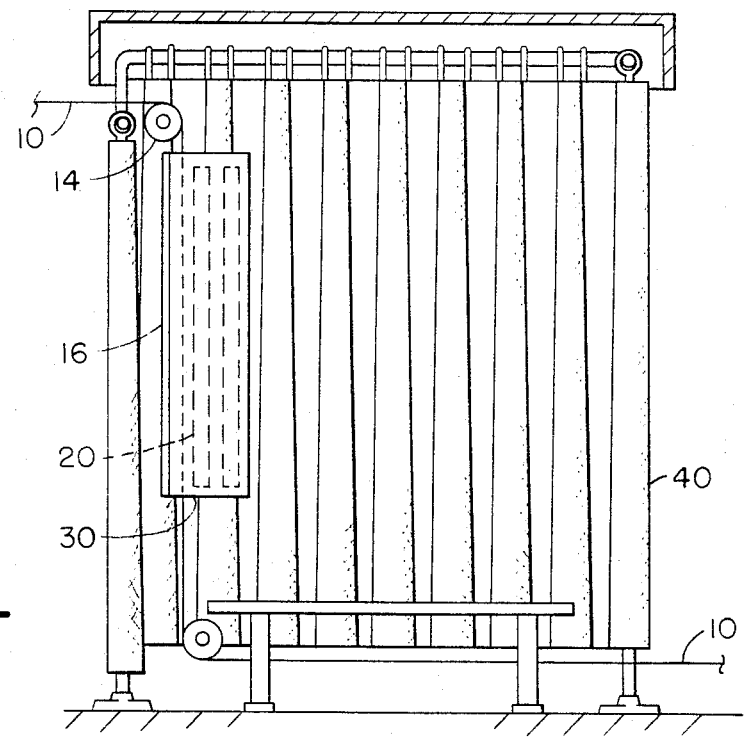
FIG. -2-

INSPECTION LIGHTING SYSTEM

This invention relates to a method and apparatus for facilitating the visual inspection of flat materials carrying an extremely shallow sculptured pattern thereon by illuminating the sculptured surface in a way which enhances the visual contrast of the pattern and renders the pattern highly visible. This invention is particularly suited for visually inspecting flat, undyed textile fabrics which carry sculptured surfaces wherein the change in the surface contour of the fabric due to the sculptured pattern is on the order of about 0.001 to about 0.003 inches.

Inspection of the finished surface of a sculptured textile substrate is a necessary function if quality control is to be maintained. Various inventions have been described in the literature for inspecting textile substrates of various kinds, for various purposes. A relatively recent example is the device described in U.S. Pat. No. 4,029,420 to Simms. The '420 device is one intended to measure light reflectance from a sample of fabric having a heterogeneous surface configuration, e.g., overlapping and intertwined threads or fibers, which is insensitive to the angular orientation of the light source and light sensor with respect to the warp and weft directions of the fabric. An odd number of light sources, preferably oriented at an angle of about 30° from the sensor aperture axis and about 60° from the plane of the fabric, are used to shine light directly onto the fabric surface, from which a light sensor measures the amount of reflected light.

U.S. Pat. No. 3,524,988 to Gaither IV discloses a method and apparatus for optically measuring the surface characteristics of a sample of fabric which has a surface in which the reflectivity can change, due to localized rearrangement of individual fibers or groups of fibers. A source of focused, monochromatic light such as a laser is used to scan the fabric surface at an angle substantially parallel to the fabric surface. The fabric surface is preferably rotated to achieve illumination over a variety of angles. An air jet or other means is used to change the fabric's topography during half of the scan cycle. The reflected laser light is measured by a sensor positioned normal to the illuminated surface. Specific applications recited include monitoring surface distortions such as pilling or distortions found in napped fabric.

U.S. Pat. No. 3,490,253 to Sick et al. is a detection scheme to detect broken or missing threads in a knitted fabric. Light is passed at a shallow angle through an aperture created by the broken or missing thread in the fabric to a detector or to a mirrored surface which reflects the light back through the aperture in the fabric to an electronic detector.

Various techniques for sculpturing pile fabrics having a wide variety of pile heights are well known in today's textile industry. This sculpturing is generally, although not always, done to produce a sculptured effect which is readily visible under ordinary room lighting conditions. It is often desirable to impart a change in the surface appearance of a flat woven or knitted fabric through, for example, differential dyeing techniques or other techniques, in which the depth of the contoured or sculptured area is extremely slight, i.e., on the order of 0.001 to 0.003 inches. Sculptured areas of this depth are usually not readily visible under ordinary room lighting conditions, particularly if the fabric has not yet been dyed, due to the extreme lack of visual contrast between the patterned and unpatterned areas. None of the systems described above, nor any system know to me other than the one described hereinbelow, is capable of inexpensively, reliably, and effectively assisting in the visual inspection of production quantities of such a "micro-sculptured" flat textile fabric, particularly if the fabric is undyed.

The apparatus and method described hereinbelow is a simple, inexpensive system for illuminating a sculptured substrate such as, for example, a textile fabric, so as to maximize the contrast between treated areas, i.e., areas which have been lightly sculptured to a depth of less than about 0.003 inches, and untreated areas. It is particularly suited to illuminating a moving web of sculptured substrate material, such as a flat, undyed textile material, as may be found at an inspection station in a textile production facility.

Details of the invention are described below, with the aid of FIGS. 1 and 2, in which:

FIG. 1 is a diagrammatic perspective view of a portion of one embodiment of the illumination system installed at an inspection station, shown without means for blocking out extraneous ambient light as it would appear in the process of inspecting a substrate web;

FIG. 2 is a diagrammatic side view of the embodiment of FIG. 1, showing a shroud for blocking out extraneous ambient light.

The apparatus depicted in FIGS. 1 and 2 are embodiments of the invention in which pairs of fluorescent tubes are used as a light source 20. Substrate 10 carrying sculptured or patterned areas 12 thereon moves over roll 14 from a finishing apparatus or storage roll, not shown, and passes over the surface of rigid support panel 16. It is preferred that the substrate 10 is made flat, in order to minimize undulations and wrinkles in the fabric which might make other, intended irregularities in the surface contour more difficult to observe. This may be achieved, for example, by applying tension to the substrate 10 by pulling or stretching substrate 10 over the smooth surface of panel member 16. Panel 16 may be substantially flat, as shown, or may be slightly convex across the width of the substrate to enhance illumination of the central portion of the substrate where side-mounted lighting is used, i.e., the curved direction of the convex panel should be perpendicular to the axis of the light source. It is preferred that panel 16 be painted with a dark, flat paint, or otherwise treated with an anti-reflective coating to reduce the reflection of light from light source 20.

The light source 20 may be fluourescent tubes, or may be incandescent bulbs of a suitable low wattage, arranged in a line array. The exact nature of the light source is not critical. The light source should generate light of sufficient intensity to illuminate the central portion of the substrate web, yet not of sufficient intensity to "wash out" the surface sculpturing found in the portions of the substrate closest to the lights. If fluorescent tubes are used, it may be necessary to reduce the light output of the tubes somewhat in order to achieve the optimum pattern resolution. This may be done by regulating the electrical power supplied to the tubes, or by other means. Lighting baffles 30 are used to prevent the light from shining directly into the eyes of the inspector, who is positioned facing the patterned surface of the substrate 10, and behind the light baffles 30.

Theoretically, it is thought that a single line source of light along each edge of the substrate web should be used; a double set of fluorescent lights is shown in FIGS. 1 and 2 because under many practical conditions, it was found that the two pairs of fluorescent lights, which had been modified by covering substantial portions of each fluorescent tube with one layer of common masking tape 21 to attenuate slightly the light output, was necessary to achieve the desired level of illumination in the central region of the substrate.

In the embodiments shown, the light sources 20 are mounted in spaced relation to the outside of the side edges of substrate 10, thereby defining a generally rectangular inspection zone extending the length of the light sources and across the width of the substrate. Generally speaking, for a substrate width of 70-80 inches, light sources 20 may be spaced about 12 to 24 inches outside the edges of the substrate, and about 4 to 10 inches from the plane of the substrate. These dimensions are suggested only; it is foreseen that other spacings may be found to be effective. Generally speaking, however, it is preferred that the angle formed between the plane of the substrate and the path of a light ray proceeding in a straight line from the light source array to the centerline of the illuminated area of the substrate be within the range of about 3 degrees and about 12 degrees. Angles nearer the lower end of this range are preferred, so long as sufficient light is directed to the central area of the substrate, and so long as the light does not "wash out" the contrast generated by the contoured areas near the edge portions of the substrate, i.e., those areas closest to the light source.

It is also preferred that the light source array used to illuminate the substrate be oriented parallel to, or at least not perpendicular to, the long axis of the principal sculptured areas on the substrate. For example, if the pattern is comprised of elongate areas, best results will be obtained if the axis of illumination, i.e., the axis of the fluorescent tubes or axis of the line array of incandescent bulbs, is parallel to the axis of the elongated patterned areas. It should be emphasized, however, that satisfactory contrast will be generated by this illumination system even if the axis of illumination is not approximately parallel to the long axis of the patterned areas, so long as the axis of illumination is not substantially perpendicular to the long axis of the patterned area. For pattern areas having no distinct long axis, e.g., areas which are substantially circular in shape, the axis of illumination may be oriented in any convenient orientation.

Where the sculptured pattern is comprised of elongate sculptured areas having axes which are perpendicular to the long edge of the substrate, and therefore perpendicular to the illumination sources shown in FIG. 1, it is desirable to move the illumination sources relative to the axes of the sculptured areas so that the illumination source is more nearly parallel to these axes, as explained above. This may be done by several means. For example, the illumination sources 20 may be mounted to panel 16, and panel 16 may be rotated slightly with respect to the axis of substrate travel in order to change the lateral angle at which the light from illumination sources 20 strikes the sculptured area. It is also foreseen that additional illumination sources may be mounted, in opposing pairs, at various angles around the area through which the substrate web to be inspected passes. For example, a set of lights may be mounted near the top and bottom of the inspection zone, in addition to those mounted at each side of the zone as shown in FIGS. 1 and 2. A given set of these opposing light sources may then be energized to the desired intensity to give the desired angle of illumination without washing out the pattern detail in the substrate area nearest the lights, while all other pairs are kept dark.

In the embodiment depicted in FIG. 2, a shroud 40 comprised of a dark, densely woven fabric or other suitable material has been shown surrounding the inspection station, including the light array. For best results, most ambient light other than light generated by the light source, i.e., "stray" light, should be shielded from the inspection station. This "stray" light tends to reduce the contrast generated by the light source. Preferably, most light striking the patterned substrate should originate with the light source. A shroud such as is depicted in FIG. 2, or similar means, may be used where ambient light levels are high; if ambient light levels are sufficiently low, such a shroud may not be necessary, or may only be needed to block out a portion of the ambient light. Generally speaking, the more ambient light is prevented from illuminating the substrate area being inspected, the more effective is the system described herein.

I claim:

1. A method for illuminating an area of a textile substrate carrying sculptured areas comprising changes in the surface contour of the substrate of less than about 0.003 inches, for the purpose of facilitating visual inspection of the sculptured areas in said area while so illuminated, said method comprising the steps of:
    (a) positioning said substrate carrying said sculptured surface in front of a visually dark, non-reflective visual background;
    (b) placing said substrate under tension to remove wrinkles and other unintended surface irregularities; and
    (c) substantially exclusively illuminating an area of said sculptured surface of said substrate with an opposed pair of light sources, each light source directing substantially all its illumination in the general direction of the opposing light source, each light source positioned so that light striking the central portion of said area of illumination does so at an angle, as measured from the plane of said substrate, of between about 3° and about 12°.

2. The method of claim 1 further comprising the step of regulating the intensity of said light sources to assure adequate illumination of said sculptured surface and prevent wash out of contrast in areas of said sculptured surfaces nearest said light sources.

3. The method of claim 1 wherein said sculptured areas have elongate portions associated therewith, and wherein said illumination is directed substantially non-parallel to said elongate portions.

4. An apparatus for illuminating an area of a textile substrate carrying sculptured areas comprising changes in the surface contour of the substrate of less than about 0.003 inches, for the purpose of facilitating visual inspection of the sculptured areas in said area while so illuminated, said apparatus comprising:
    (a) visually dark, non-light reflective background means against which said sculptured surface may be positioned and viewed;
    (b) means for placing said substrate under tension to remove wrinkles and other unintended surface irregularities; and
    (c) means for substantially exclusively illuminating an area of said sculptured surface of said substrate, said means comprising an opposed pair of light sources, each light source serving as a line array and directing substantially all its illumination in the general direction of the opposing light source, each light source positioned so that light striking the central portion of said area of illumination does so at an angle, as measured from the plane of said substrate, of between about 3° and about 12°.

5. The apparatus of claim 4 wherein said background means comprises a rigid panel means.

6. The apparatus of claim 4 further comprising shroud means for shielding ambient light from said illuminated area.

7. The apparatus of claim 4 further comprising means for regulating the intensity of said light sources to assure adequate illumination of said sculptured surface and prevent wash out of contrast in areas of said sculptured surfaces nearest said light sources.

* * * * *